United States Patent
Pöchlauer et al.

(10) Patent No.: US 6,717,006 B1
(45) Date of Patent: Apr. 6, 2004

(54) METHOD FOR THE PRODUCTION OF OPTICALLY ACTIVE CYANOHYDRINS USING R-OXYNITRILASE

(75) Inventors: Peter Pöchlauer, Linz (AT); Irma Wirth, Linz (AT); Herbert Mayrhofer, Engerwitzdorf (AT); Rudolf Neuhofer, Mittertreffling (AT)

(73) Assignee: DSM Fine Chemicals Austria Nfg GmbH & Co KG, Linz (AT)

( * ) Notice: Subject to any disclaimer, the term of this patent is extended or adjusted under 35 U.S.C. 154(b) by 25 days.

(21) Appl. No.: 10/149,186

(22) PCT Filed: Nov. 25, 2000

(86) PCT No.: PCT/EP00/11753

§ 371 (c)(1),
(2), (4) Date: Jun. 10, 2002

(87) PCT Pub. No.: WO01/44487

PCT Pub. Date: Jun. 21, 2001

(30) Foreign Application Priority Data

Dec. 15, 1999 (AT) .......................................... A 2108/99

(51) Int. Cl.[7] .............................. C12P 13/00; C12N 9/88
(52) U.S. Cl. ....................................... 558/351; 435/128
(58) Field of Search ........................... 558/351; 435/128

(56) References Cited

FOREIGN PATENT DOCUMENTS

| DE | 40 08 412 | 7/1991 |
|---|---|---|
| DE | 41 02 327 | 6/1992 |
| DE | 195 06 728 | 8/1996 |
| DE | 197 03 314 | 8/1997 |
| EP | 0 276 375 | 8/1988 |
| EP | 0 547 655 | 6/1993 |
| EP | 0 927 766 | 7/1999 |
| WO | 99/63104 | 12/1999 |

OTHER PUBLICATIONS

Effenberger et al., Angewandte Chemie International Edition in English, vol. 26, No. 5, pp. 458–460 (1987)—XPOO2165559.

Ognyanov et al., Journal of the American Chemical Society, vol. 113, No. 18, pp. 6992–6996 (1991)—XPOO2165560.

Primary Examiner—Joseph K. McKane
Assistant Examiner—Kamal Saeed
(74) Attorney, Agent, or Firm—Wenderoth, Lind & Ponack, LLP

(57) ABSTRACT

The invention relates to the production of (R)-enantiomeric, optically active cyanohydrins by reacting an aldehyde or a ketone with a cyanide group donor in the presence of (R) oxynitrilase, wherein a reaction mixture comprising a) an aldehyde or a ketone dissolved in an organic solvent; said organic solvent is immiscible or only slightly miscible with water, b) any aqueous R)-oxynitrilase solution and c) a cyanide group donor is stirred in such away that an emulsion is formed which remains intact until the end of the enzymatic reaction. After the enzymatic reaction has terminated, the (R)-cyanohydrin is isolated from the reaction mixture.

9 Claims, No Drawings

METHOD FOR THE PRODUCTION OF OPTICALLY ACTIVE CYANOHYDRINS USING R-OXYNITRILASE

Cyanohydrins are of importance, for instance, for the synthesis of alpha-hydroxyacids, alpha-hydroxyketones, beta-aminoalcohols, which are used to produce biologically active substances, for example active pharmaceutical substances, vitamins or pyrethroid compounds.

A cyanohydrin can be produced by addition of hydrocyanic acid (HCN) to the carbonyl group of an aldehyde or of an unsymmetrical ketone, enantiomeric mixtures of unsymmetrical cyanohydrins being formed.

Since in a biologically active enantiomeric mixture usually only one of the two enantiomers is biologically active, there has been no lack of attempts to find a method for producing the (R)-enantiomer of an optically active cyanohydrin in the highest possible optical purity.

Many methods are based on adding HCN to the carbonyl group in the presence of a chiral catalyst, for example an oxynitrilase.

The enantiomeric purity of the cyanohydrin to be synthesized depends to a great extent on how much the competing chemical reaction and racemization can be suppressed.

As is disclosed by J. Am. Chem. Soc. 1991, 113, pp. 6992–6996, particularly in the case of methods employing an aqueous system it is difficult, because of this competing reaction, to achieve high enantioselectivity and enantiomeric purity.

One way of suppressing the competing chemical reaction and racemization is disclosed in EP-A-0 326 063, according to which optically active (R)-cyanohydrins are said to be obtained by reacting aliphatic, aromatic or heteroaromatic aldehydes or ketones in an aqueous environment with hydrocyanic acid in the presence of (R)-oxynitrilase (EC 4.1.2.10) from Prunus amygdalus, by employing acidic conditions, in particular pH$\leq$4.5, at temperatures such that the competing chemical reaction and racemization are negligible compared with the enzymatic synthesis. Reference is made here to the increased activity losses of the biocatalyst under these conditions and the examples show favoring of low temperatures in the range from 5 to 8° C.

Since the enzymes are water-soluble proteins and the substrates, in contrast, are only sparingly water-soluble compounds, the use of water-miscible organic solvents to improve the solubility of the substrate and the product has been proposed.

Thus, for example, Effenberger et al. (Angew. Chem. 99 (1987) pp. 491–492) studied enzymatic cyanohydrin formation in aqueous alcoholic systems varying the pH, temperature and concentration with a view to optimum suppression of the competing reactions. However, the stereochemical purity of the desired end products was frequently unsatisfactory. As an improvement it was proposed to carry out the enzymatic reaction of oxo compounds with hydrocyanic acid in organic water-immiscible solvents in order to suppress the chemical reaction. In this case, preferably ethyl acetate and support-immobilized (R)-oxynitrilase were employed. Although in this manner products of high optical purity were obtained, as a result of the enzyme immobilization, a considerable loss of enzyme activity was observed. In addition, it was found that the non-enzymatic reaction which leads in the aqueous phase, by addition of hydrocyanic acid to the starting compound, to racemic cyanohydrins, causes an unwanted decrease in enantiomeric purity of the product.

In J. Am. Chem. Soc. 1991, 113, pp. 6992–6996 the problems associated with the use of free hydrocyanic acid are avoided by a transcyanation in the presence of hydroxynitrilase using acetone cyanohydrin in a two-phase reaction mixture consisting of an aqueous buffer solution and a water-immiscible solvent. The disadvantage in this case is that the volume of organic solvent, and as a result of the entire reaction mixture, is somewhat large in relation to the amount of aldehyde used. In addition, an extremely long reaction time and a large amount of enzyme are required. Finally, the optical purity of the cyanohydrins is also generally inadequate for enantiospecific synthesis of the target products.

As an improvement, EP-A1-0 547 655 proposes a method in which optically active cyanohydrins are produced from aldehydes or ketones and hydrocyanic acid in a two-phase system consisting of a homogeneous aqueous solution of the hydroxynitrilase and a suitable organic solvent which is at least essentially immiscible with water, the aqueous solution being buffered by an acetate buffer at a concentration of 0.005 to 0.1 mol per liter, and the ratio of organic phase to aqueous phase being between 5:1 and 1:5. The reaction system is stirred during the enzymatic reaction, the two-phase system being maintained.

Despite the reaction at a pH of about 4.5, the chemical reaction, however, cannot be suppressed completely, even in this two-phase system of organic substrate solution and aqueous enzyme solution. A disadvantage with this method is that the ee values of the cyanohydrins could only be improved by using large amounts of enzyme.

It was an object of the invention to find an improved method for the production of optically active cyanohydrins which ensures high enantiomeric purity with at the same time low enzyme and time requirements.

It has now unexpectedly been found that it is possible to react a multiplicity of carbonyl compounds, for instance aliphatic, alicyclic, unsaturated, aromatically substituted aliphatic, aromatic and heteroaromatic aldehydes and ketones, to give the corresponding cyanohydrins with high yield and at high optical purity in a more concentrated procedure, with lower enzyme usage and in with shorter reaction times, compared with the prior art, if the reaction is carried out in an emulsion. Unexpectedly, the enzyme activity remains stable under emulsion conditions which lead, with many proteins, to deactivation, such as in the case of high stirring energy.

The present invention therefore relates to a method for the production of (R)-enantiomers of optically active cyanohydrins by reacting an aldehyde or a ketone with a cyanide group donor in the presence of an (R)-oxynitrilase which is characterized in that a reaction mixture of a) an aldehyde or ketone dissolved in an organic, water-immiscible or only slightly water-miscible diluent, b) an aqueous (R)-oxynitrilase solution and c) a cyanide group donor is stirred in such a manner that an emulsion forms which is maintained up to the end of the enzymatic reaction, whereupon, after the enzymatic reaction is terminated, the corresponding (R)-cyanohydrin is isolated from the reaction mixture.

The starting materials used in the inventive method are an aldehyde or a ketone, a cyanide group donor, an aqueous solution of an (R)-oxynitrilase and an organic water-immiscible or only slightly water-miscible diluent.

Aldehydes are taken to mean here aliphatic, aromatic or heteroaromatic aldehydes. Aliphatic aldehydes are taken to mean saturated or unsaturated, aliphatic, unbranched, branched or cyclic aldehydes. Preferred aliphatic aldehydes are unbranched aldehydes having, in particular, 2 to 30 carbon atoms, preferably 2 to 18 carbon atoms, which are saturated or are monounsaturated or polyunsaturated. The aldehyde can have not only C—C double bonds but also C—C triple bonds. The aliphatic, aromatic or heteroaromatic aldehydes can, in addition, be unsubstituted or be substituted by groups inert under the reaction conditions, for example by unsubstituted or substituted aryl or heteroaryl groups, such as phenyl, phenoxy or indolyl groups, by halogen, hydroxyl, hydroxy-$C_1$–$C_5$ alkyl, $C_1$–$C_5$ alkoxy, $C_1$–$C_5$ alkylthio, ether, alcohol, carboxylic ester, nitro or azido groups.

Examples of aromatic or heteroaromatic aldehydes are benzaldehyde and variously substituted benzaldehydes, for instance 3,4-difluorobenzaldehyde, 3-phenoxybenzaldehyde, 4-fluoro-3-phenoxybenzaldehyde, hydroxybenzaldehyde, methoxybenzaldehyde, in addition furfural, methylfurfural, anthracene-9-carbaldehyde, furan-3-carbaldehyde, indole-3-carbaldehyde, naphthalene-1-carbaldehyde, phthaldialdehyde, pyrazole-3-carbaldehyde, pyrrole-2-carbaldehyde, thiophene-2-carbaldehyde, isophthalaldehyde or pyridinealdehydes, thienylaldehydes, etc.

Ketones are aliphatic, aromatic or heteroaromatic ketones in which the carbonyl carbon is unequally substituted. Aliphatic ketones are taken to mean saturated or unsaturated, unbranched, branched or cyclic ketones. The ketones can be saturated or monounsaturated or polyunsaturated. They can be unsubstituted, or substituted by groups inert under the reaction conditions, for example by unsubstituted or substituted aryl or heteroaryl groups such as phenyl or inolyl groups, by halogen, ether, alcohol, carboxylic ester, nitro or azido groups.

Examples of aromatic or heteroaromatic ketones are acetophenone, indolylacetone, etc.

Aldehydes and ketones which are suitable for the inventive method are known or can be produced by conventional means.

The cyanide group donor added is hydrocyanic acid. The hydrocyanic acid here can also be released shortly before the reaction from one of its salts, for instance NaCN or KCN, and added to the reaction mixture without solvent or in dissolved form.

Suitable oxynitrilases are (R)-oxynitrilases, for example, from Prunus amygdalus, Prunus laurocerasus or Prunus serotina. Preferably, the oxynitrilase used is oxynitrilase from Prunus amygdalus.

The enzyme is distinguished by a high resistance to solvents. Therefore, there is the possibility of using for the enzymatic reaction various organic solvents which permit the formation of an emulsion which has a beneficial action on the productivity of the respective process.

The oxynitrile lyase can be used in the purified or unpurified form, as such or immobilized.

The organic diluent used can be water-immiscible or only slightly water-miscible aliphatic or aromatic hydrocarbons which may be halogenated, alcohols, ethers or esters or mixtures thereof. Examples of these are diethyl ether, diisopropyl ether, dibutyl ether, methyl tert-butyl ether, ethyl acetate, propyl acetate, toluene, xylene, cyclohexane, trichloroethane, chlorobenzene, etc.

Preferably, methyl tert-butyl ether (MTBE), diisopropyl ether, dibutyl ether and ethyl acetate or a mixture of MTBE and toluene are used.

About 0.2 to 20 g of diluent and 10 to 2000 IU of activity of oxynitrilase, preferably about 50 to 1000 IU, are added per g of aldehyde or ketone.

One IU (International Unit) is that amount of an enzyme preparation which catalyzes the formation of one micromole of product per minute. The required amount of the respective oxynitrilase is best determined in an activity assay, for example by the activity assay of Sigma, similar to that of Jorns et al. J. Biolog. Chem. 254, pp. 12145–12152, 1979.

At least 1 mole, preferably 1 to 5 moles, particularly preferably 1 to 2 moles, of cyanide group donor are added per mole of aldehyde or keto group used. In the inventive method the aldehyde or the ketone is dissolved in the organic diluent. To this solution the enzyme is added in the form of an aqueous buffer solution. The pH of this solution is to be in this case less than 7, preferably between 3 and 6.5.

The resultant reaction mixture is stirred at temperatures of 0 to about 30° C., preferably 5 to 25° C., in such a manner that an emulsion forms. The stirrer speed (N) required for this depends on what is termed the power number of the stirrer used (Po), its diameter (d), the reaction volume (V) and the density (ρ) of the reaction medium. From these factors may be calculated the stirrer energy (P/V), that is to say the stirrer power per unit of reaction volume (volume of the reaction mixture, not of the apparatus).

$$P/V = \frac{P_0 \cdot \rho \cdot N^3 \cdot d^3}{V}$$

Preferably, the stirrer energy in the inventive process is, greater than 500 W/m$^3$, particularly preferably greater than 1000 W/m$^3$. By way of comparison, in the case of previously known methods which operate in an aqueous, organic or two-phase system, for instance according to EP-A1-0 547 655, stirrer energies merely of approximately 100 W/m$^3$ are achieved.

If the reaction mixture is an emulsion, the cyanide group donor is added. The emulsion is maintained until the end of the reaction. The course of the reaction can be followed, for example, photometrically via the decrease in aldehyde or ketone content.

Depending on the starting material, measurements are made at the wavelength at which the starting material absorbs and the resultant cyanohydrin does not absorb. The absorption of the reaction mixture thus decreases in proportion with increasing conversion.

However, all components may first be mixed and then the resultant reaction mixture may be stirred in such a manner that an emulsion is obtained.

When a salt of hydrocyanic acid is used, the hydrocyanic acid can first be released from a solution of the salt by adding, for example, $H_2SO_4$ or $H_3PO_4$. The pH of this solution of hydrocyanic acid should be less than 7, preferably between 4 and 6.5.

The aqueous enzyme solution, the organic diluent and the aldehyde or the ketone are then added to the hydrocyanic acid solution, the reaction is started and if appropriate the pH is readjusted.

Here also, it must be ensured that the reaction mixture is stirred in such a manner that an emulsion forms which in turn remains until the end of the reaction.

For workup of the reaction mixture and to isolate the cyanohydrin formed, customary methods are used which first break the emulsion, for example filtration, centrifugation or coalescence. The resultant phases are then separated, if appropriate with addition of demulsifiers, and the product-containing phase is worked up.

To obtain the corresponding cyanohydrin, depending on the end product, known methods such as filtration, distillation, extraction or crystallization are employed. The cyanohydrins thus obtained can, if appropriate, be stabilized by adding an acid before further processing.

EXAMPLE 1

2-Chlorobenzaldehyde 0.25 to 1 ml of R-oxynitrilase solution (E.C. 4.1.2.10, 877 units/ml) were diluted to 4 ml with 50 mM citrate/phosphate buffer (pH 4) and the pH of the enzyme solution was adjusted to pH 4, if appropriate, using a few drops of citric acid solution. To this solution was added a solution of 3 ml of t-butyl methyl ether and 0.8 g (5.69 mmol) of 2-chlorobenzaldehyde and then 445 μl (11.38 mmol) of hydrocyanic acid were added. The reaction mixture was stirred at room temperature using a magnetic stirrer at 500 and 900 rpm. If stirring was performed at 500 rpm (comparative experiments), a two-phase system similar to EP-A1-0 547 655 was present, whereas stirring at 900 rpm formed an emulsion.

The conversion rate and the enantiomeric purity of the (R)-cyanohydrin formed were analyzed by GC.

For this a sample of the reaction solution was centrifuged and 50 μl of the organic phase was diluted with dichloromethane. After derivatization with acetyl chloride, the product was analyzed by gas chromatographyon a cyclodextrin column.

The conversion rate and the enantiomeric purity can be seen in tables 1 and 2 as a function of the amount of enzyme and the stirrer speed (two-phase system or emulsion).

TABLE 1

Two-phase System (comparative experiment)

| Time (h) | 0.25 ml of enzyme solution/ 500 rpm | | 0.5 ml of enzyme solution/ 500 rpm | | 1.0 ml of enzyme solution/ 500 rpm | |
|---|---|---|---|---|---|---|
| | % conversion | % ee | % conversion | % ee | % conversion | % ee |
| 0 | 0 | | 0 | | 0 | |
| 0.5 | 21.6 | 68.2 | 16.8 | 70 | 25.5 | 83.7 |
| 1 | 39.2 | 68.6 | 53.8 | 76.5 | 56.3 | 85.5 |
| 1.5 | 52.2 | 68.1 | 67.6 | 76.5 | 85.9 | 86.4 |
| 2 | 54.3 | 67.7 | 78.4 | 76.5 | 85.6 | 86.5 |
| 3 | 51.5 | 66.6 | 84.2 | 76.4 | 93.8 | 86.4 |
| 3.5 | 71.6 | 66.3 | 86.6 | 76.3 | 96.8 | 86.3 |
| 4.5 | 78.2 | 65.8 | 92.3 | 76.4 | 98.7 | 86.0 |

TABLE 2

Emulsion

| Time (h) | 0.25 ml of enzyme solution/ 900 rpm | | 0.5 ml of enzyme solution/ 900 rpm | | 1.0 ml of enzyme solution/ 900 rpm | |
|---|---|---|---|---|---|---|
| | % conversion | % ee | % conversion | % ee | % conversion | % ee |
| 0 | 0 | | 0 | | 0 | |
| 0.5 | | | | | | |
| 1 | | | | | | |
| 1.5 | 79.1 | 77.5 | 97.6 | 81.6 | 98.7 | 89.4 |
| 2 | | | | | | |
| 3 | 98 | 77.4 | 100 | 81.5 | 100 | 89.1 |
| 3.5 | | | | | | |
| 4.5 | | | | | | |

EXAMPLE 2 n-Butyraldehyde 1 ml of R-oxynitrilase solution (E.C. 4.1.2.10, 877 units/ml) was diluted to 4 ml with 50 mM citrate/phosphate buffer (pH 4) and the pH of the enzyme solution was adjusted to pH 4, if appropriate, using a few drops of citric acid solution. To this solution was added a solution of 3 ml of t-butyl methyl ether and 0.8 g (11 mmol) of n-butyraldehyde, and then 860 μl (22 mmol) of hydrocyanic acid were added. The reaction mixture was stirred at room temperature using a magnetic stirrer at 900 rpm, as a result of which an emulsion formed.

The conversion rate and the enantiomeric purity of the cyanohydrin formed were analyzed by GC.

For this a sample of the reaction solution was centrifuged and 50 μl of the organic phase were diluted with dichloromethane. After derivatization with acetyl chloride, the product was analyzed by gas chromatography on a cyclodextrin column.

After 5 minutes the aldehyde was completely converted to the corresponding (R)-cyanohydrin at an enantiomeric purity of 98%.

What is claimed is:

1. A method for the production of (R)-enantiomers of optically active cyanohydrins by reacting an aldehyde or a ketone with a cyanide group donor in the presence of an (R)-oxynitrilase, characterized in that a reaction mixture of a) an aldehyde or ketone dissolved in an organic, water-immiscible or only slightly water-miscible diluent, b) an aqueous (R)-oxynitrilase solution and c) a cyanide group donor is stirred in such a manner that an emulsion forms which is maintained up to the end of the enzymatic reaction, whereupon, after the enzymatic reaction is terminated, the corresponding (R)-cyanohydrin is isolated from the reaction mixture.

2. The method as claimed in claim 1, characterized in that an aliphatic, aromatic or heteroaromatic aldehyde or an unsymmetrical ketone is reacted.

3. The method as claimed in claim 1, characterized in that the cyanide group donor added is hydrocyanic acid.

4. The method as claimed in claim 1, characterized in that the oxynitrilase used is an (R)-oxynitrilase from Prunus amygdalus.

5. The method as claimed in claim 1, characterized in that water-immiscible or only slightly water-miscible aliphatic or aromatic hydrocarbons which may be halogenated, alcohols, ethers or esters or mixtures are used as diluent.

6. The method as claimed in claim 1, characterized in that the diluent used is methyl tert-butyl ether, diisopropyl ether, dibutyl ether, ethyl acetate or a mixture of methyl tert-butyl ether and toluene.

7. The method as claimed in claim 1, characterized in that the reaction temperature is 0° C. to 30° C.

8. The method as claimed in claim 1, characterized in that after the enzymatic reaction is completed, to isolate the corresponding (R)-cyanohydrin from the reaction mixture, the emulsion is first broken by filtration, centrifugation or coalescence and the phases forming are then separated, if appropriate with addition of demulsifiers, and the product-containing phase is worked up.

9. The method as claimed in claim 8, characterized in that the product-containing phase, depending on the end product, is worked up by filtration, distillation, extraction or crystallization.

* * * * *